US012599291B2

(12) United States Patent
Forster et al.

(10) Patent No.: US 12,599,291 B2
(45) Date of Patent: Apr. 14, 2026

(54) OPTICAL INSTRUMENT CONFIGURED TO SWITCH BETWEEN AN INTEGRATED AND EXTERNAL LIGHT SOURCE

(71) Applicant: Karl Storz SE & Co. KG, Tuttlingen (DE)

(72) Inventors: Jonas Forster, Tuttlingen (DE); Andreas Heni, Fridingen (DE); Pascal Heni, Fridingen (DE); Marcus Kupferschmid, Emmingen-Liptingen (DE); Daniel Ulmschneider, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 234 days.

(21) Appl. No.: 18/562,684

(22) PCT Filed: May 19, 2022

(86) PCT No.: PCT/EP2022/063506
§ 371 (c)(1),
(2) Date: Nov. 20, 2023

(87) PCT Pub. No.: WO2022/248320
PCT Pub. Date: Dec. 1, 2022

(65) Prior Publication Data
US 2024/0237883 A1 Jul. 18, 2024

(30) Foreign Application Priority Data
May 26, 2021 (DE) ..................... 10 2021 113 615.6

(51) Int. Cl.
*A61B 1/06* (2006.01)
*A61B 1/00* (2006.01)
(Continued)

(52) U.S. Cl.
CPC ...... *A61B 1/00126* (2013.01); *A61B 1/00029* (2013.01); *A61B 1/0669* (2013.01); *A61B 1/07* (2013.01); *G02B 23/2469* (2013.01)

(58) Field of Classification Search
None
See application file for complete search history.

(56) References Cited

U.S. PATENT DOCUMENTS 3,775,606 A * 11/1973 Bazell ..................... F21V 29/60
362/572
4,061,911 A * 12/1977 Krasin ................... H05B 39/10
352/198
(Continued)

FOREIGN PATENT DOCUMENTS

DE 3920494 A1 1/1991
JP H10-165367 A 6/1998

OTHER PUBLICATIONS

WIPO International Preliminary Report on Patentability, Application No. PCT/EP2022/063506, issued Nov. 21, 2023.
(Continued)

*Primary Examiner* — John P Leubecker
(74) *Attorney, Agent, or Firm* — Brooks Kushman PC

(57) ABSTRACT

Disclosed is an optical instrument having a housing, wherein situated in the housing is a light source which is designed to generate a first light flux which exits at a first interface inside the housing, and a light supply which is designed to guide a second light flux from outside the housing into an interior of the housing and to allow said light flux to exit at a second interface inside the housing; wherein situated in the housing is a light guide which is designed to receive, either from the first interface or from the second interface, light at a first end via a third interface.

12 Claims, 8 Drawing Sheets

(51) Int. Cl.
    *A61B 1/07*         (2006.01)
    *G02B 23/24*       (2006.01)

(56) References Cited

U.S. PATENT DOCUMENTS

| | | | | |
|---|---|---|---|---|
| 4,919,114 A * | 4/1990 | Miyazaki | ........... | G02B 23/2476 |
| | | | | 600/110 |
| 6,494,899 B1 * | 12/2002 | Griffin | ................. | A61N 5/0621 |
| | | | | 607/90 |
| 2004/0210112 A1 * | 10/2004 | Ota | ...................... | A61B 1/0684 |
| | | | | 600/178 |
| 2006/0241347 A1 * | 10/2006 | Whitehead | ......... | A61B 1/00096 |
| | | | | 600/129 |
| 2008/0228038 A1 * | 9/2008 | McMahon | ............ | A61B 1/303 |
| | | | | 600/223 |
| 2008/0298044 A1 * | 12/2008 | Chen | ................. | G03B 21/2086 |
| | | | | 362/20 |
| 2009/0232448 A1 * | 9/2009 | Barmash | .............. | G02B 6/3504 |
| | | | | 385/26 |
| 2010/0022829 A1 * | 1/2010 | Irion | ................. | A61B 1/00124 |
| | | | | 600/109 |
| 2017/0245745 A1 * | 8/2017 | Ohara | .................. | A61B 1/0661 |
| 2017/0280037 A1 | 9/2017 | Sakai et al. | | |
| 2018/0317758 A1 * | 11/2018 | Okada | ..................... | A61B 90/30 |
| 2022/0043274 A1 * | 2/2022 | Moore | ................ | G03B 21/208 |

OTHER PUBLICATIONS

Written Opinion of the International Searching Authority, Application No. PCT/EP2022/063506, mailed dated Aug. 18, 2022.
International Search Report, Application No. PCT/EP2022/063506, mailed Aug. 18, 2022. ISA/European Patent Office.

* cited by examiner

10

34

32

12

42

18    20    46

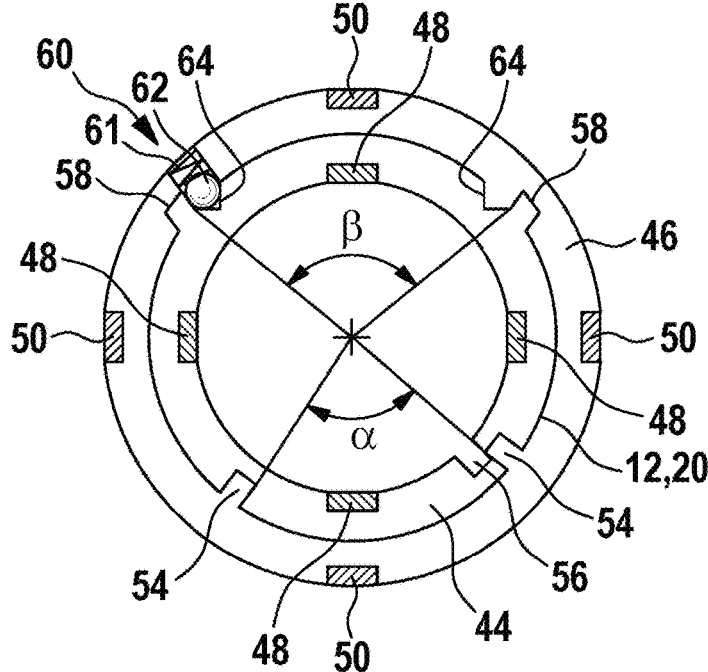
Fig. 10
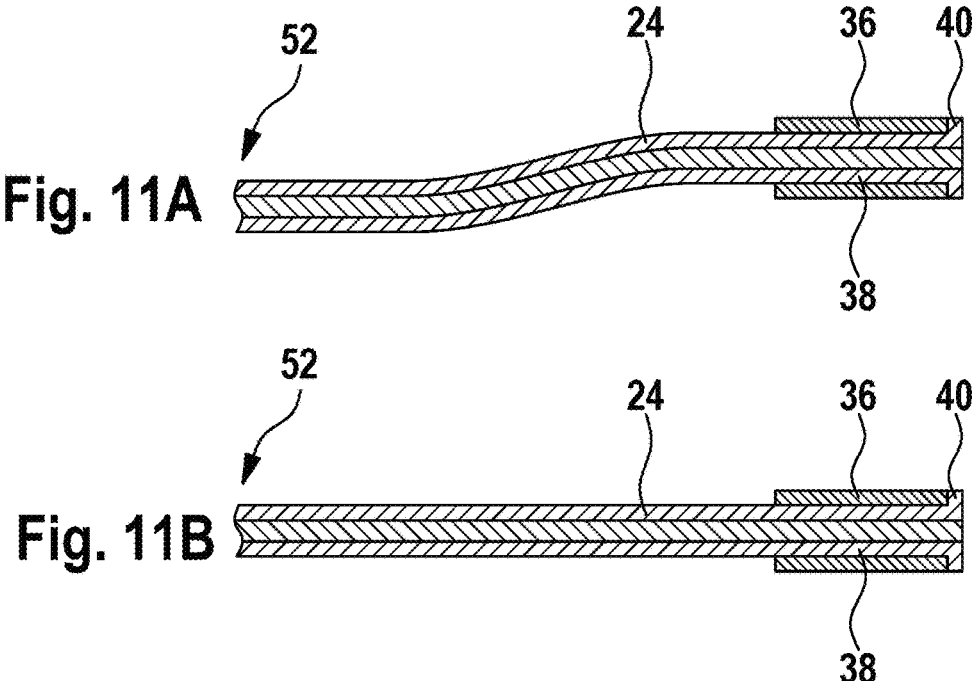
Fig. 11A
Fig. 11B

OPTICAL INSTRUMENT CONFIGURED TO SWITCH BETWEEN AN INTEGRATED AND EXTERNAL LIGHT SOURCE

CROSS-REFERENCE TO RELATED APPLICATIONS

This application is the U.S. national stage of PCT/EP2022/063506 filed on May 19, 2022, which claims priority of German Patent Application No. DE 10 2021 113 615.6 filed on May 26, 2021, the contents of which are incorporated herein.

TECHNICAL FIELD

The invention relates to an optical instrument, in particular an endoscope or an exoscope.

BACKGROUND

Optical instruments, endoscopes for example, generally have an integrated lighting system, especially one or more LEDs in the housing of the endoscope. Alternatively, endoscopes with an external light supply or external light connector are known. At the light connector, light can be guided into the endoscope from an external light source by means of a light cable and can be transmitted from there to the distal end of the endoscope by means of optical fibers.

SUMMARY

It is an object of the present invention to specify an improved optical system which offers greater flexibility in relation to the lighting options.

The object is achieved by an optical instrument having a housing, wherein the housing accommodates a light source designed to create a first light flux that emerges at a first interface within the housing, and a light supply from outside of the housing is guided through a housing wall of the housing and designed to guide a second light flux from outside of the housing into an interior of the housing and allow said light flux to emerge at a second interface within the housing, with the housing accommodating a light guide designed to receive light at a first end via a third interface and allow said light to emerge at a second end via a fourth interface at a distal end of the optical instrument, with the third interface being displaceably arranged relative to the first and the second interface such that the third interface can receive light from the first interface in a first position and receive light from the second interface in a second position.

This makes it possible to use at least two different lighting systems in an optical instrument and use said lighting systems alternately. It is also possible to switch the respective lighting system on or off, depending on the position of the third interface.

Firstly, lighting can be brought about by way of an external light source that is connected to the optical instrument via the light supply, in particular a light cable. Alternatively, lighting is brought about by way of the integrated light source, in particular one or more LEDs. In this case, the power supply of the light source can be implemented in particular via the data cable usually present in video endoscopes.

A switching apparatus has been attached to the optical instrument for the purpose of changing between the first and second position and can be used to switch the light guide situated in the optical instrument back and forth, with the result that said light guide either is optically coupled to the light from the light source present internally in the optical instrument or is supplied from an external light source by way of the light connector present. Thus, the user can switch between different lighting systems using one and the same device, resulting in a great degree of flexibility.

Depending on the user requirement, it is possible to dispense with a light cable connected to the optical instrument in the case of the lighting mode by means of the internal light source. Should the user require a higher luminous intensity or a light that cannot be provided by the internal light source, for example light at a specific wavelength, it is possible to connect an external light source to the optical instrument by means of the light supply, in particular a light cable. In the process, it is possible to switch between the various light sources, for example by means of a mechanical, magnetic or electric switch.

The internal light source can be arranged in the shaft or in the handle of the optical instrument, each of these being able to be a separate, couplable part of the optical instrument. The light supply, in particular a light connector, for the external light source may be placed in the shaft or in the handle, each of these yet again being able to be a separate, couplable part of the optical instrument.

This completely achieves the object.

BRIEF DESCRIPTION OF DRAWINGS

FIG. 10 shows a schematic illustration of the rings of the embodiment, in cooperation with the housing;

FIG. 11A shows a schematic illustration of the functionality of a sleeve in the embodiment, with the rings in one of the first and the second positions;

FIG. 11B shows a schematic illustration of the functionality of a sleeve in the embodiment, with the rings in the intermediate position;

DETAILED DESCRIPTION OF PREFERRED EMBODIMENTS

Figure 1:
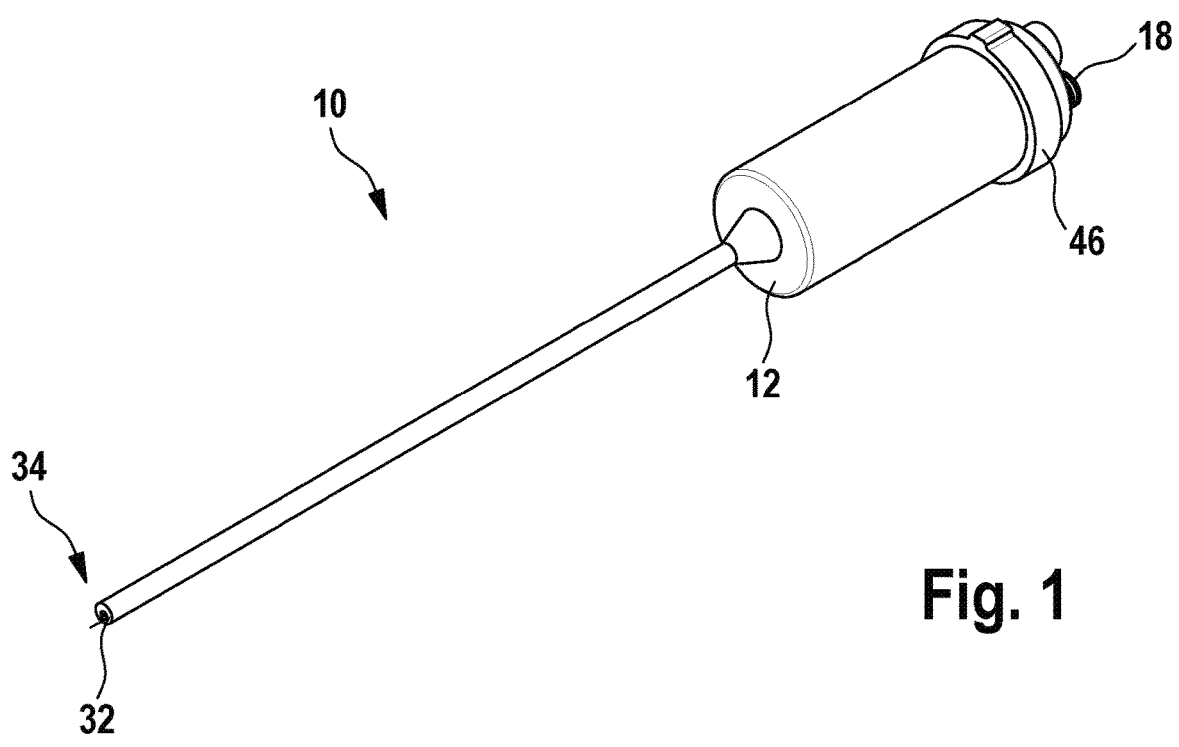
FIG. 1 shows an embodiment of an endoscope in a first perspective view.

In a preferred configuration, the first end of the light guide is linearly displaceably held in a guide.

This configuration allows the first end of the light guide to be displaced by a certain amount when the third interface is displaced from the first to the second position, and vice versa. As a rule, the light guide needs to be held at a defined location or fixed point within the housing of the optical instrument. The profile of the light guide from the fixed point can change in the direction of the first end during the displacement from the first to the second position, and vice versa. The linear displaceability makes it possible to offset the degree of freedom of this change without a mechanical load on the light guide.

In a further preferred configuration, the first end comprises a sleeve and the sleeve is linearly displaceably held in the guide.

This configuration enables a good displaceability of the first end.

In a further preferred configuration, the guide and the sleeve are cylindrical.

This configuration offers a further degree of freedom since the first end is now able to rotate within the guide.

In a further preferred configuration, the sleeve comprises a flange which forms a stop for a displacement of the sleeve.

This configuration enables a defined displacement of the sleeve. In this case, the stop may limit a displacement in the proximal or distal direction. If two stops are used on the sleeve, then it is possible to limit a displacement in both the proximal and distal direction. Moreover, the sleeve, and hence the first end, has a defined position at the stop.

In a further preferred configuration, the light source is supplied with power via a power supply which is guided from outside of the housing through the housing wall of the housing.

This configuration enables a reliable power supply for the internal light source. If a power supply is already present, for example within a voltage supply for an image sensor in the optical instrument, then this existing power supply can also be used to supply power for the internal light source.

In a further preferred configuration, the first end is arranged within the housing on an inner ring that is rotatably arranged about a longitudinal axis of the optical instrument.

This configuration enables a guided displaceability of the first end.

In a further preferred configuration, the optical instrument further comprises an outer ring that is arranged outside of the housing and is rotatably arranged about the longitudinal axis of the optical instrument, with at least one first magnet being arranged on the inner ring, at least one second magnet being arranged on the outer ring, and the first magnet and the second magnet interacting such that a rotation of the outer ring can bring about a rotation of the inner ring.

This configuration enables a displacement of the inner ring by way of an actuation from the outside, without needing to provide an opening in the housing to this end. In this case, first and second magnets with opposite poles in particular are opposite one another, with the result that the first and second magnets interact such that a distance between the first and second magnets is as small as possible.

In a further preferred configuration, the housing comprises two inwardly directed first stops, which interact with a first protrusion on the inner ring and limit a displacement of the inner ring to a first angular range, and the housing comprises two outwardly directed second stops, which interact with a second protrusion on the outer ring and limit a displacement of the outer ring to a second angular range, the second angular range being greater than the first angular range.

This configuration allows the protrusion of the inner ring to be pulled against one of the first stops with a certain force and thus attain a good fixation of the inner ring in its position. To this end, first and second magnets with opposite poles are opposite one another. Since the outer ring can be rotated further than the inner ring is able to follow, the magnets exert the certain force for pulling the inner ring against one of the first stops and thus fix said inner ring.

In a further preferred configuration, the second protrusion has a catch which is pressed inwardly against the housing by means of a spring, and this catch interacts with at least one cutout in the housing in order to detachably fix the outer ring in at least one defined position.

This configuration allows the outer ring to be fixed at at least one defined position. Moreover, haptic feedback can be obtained by the catch latching in the cutout.

In a further preferred configuration, the light supply and/or the light guide is an optical waveguide.

It is understood that the features described hereinabove and hereinbelow can be used not only in the expressly stated combinations, but also in other combinations and also in isolation.

Exemplary embodiments of the invention are depicted in the drawing and are described in more detail in the following description. In the drawing:

In conjunction with FIGS. 2 to 5, FIG. 1 shows an endoscope 10, as an example of an optical instrument, having a housing 12, the housing 12 accommodating a light source 14. The light source 14 is designed to create a first light flux that emerges at a first interface 16 within the housing 12. An exoscope represents a further example of an optical instrument.

A light supply 18 is guided from outside of the housing 12 through a housing wall 20. The light supply 18 is designed to guide a second light flux from outside of the housing 12 into an interior of the housing 12 and allow said light flux to emerge at a second interface 22 (see FIG. 8) within the housing 12.

The housing 12 accommodates a light guide 24 designed to receive a light at a first end 26 via a third interface 28 (see FIG. 5) and allow said light to emerge at a second end 30 via a fourth interface 32 at a distal end 34 of the endoscope 10.

Figure 3:
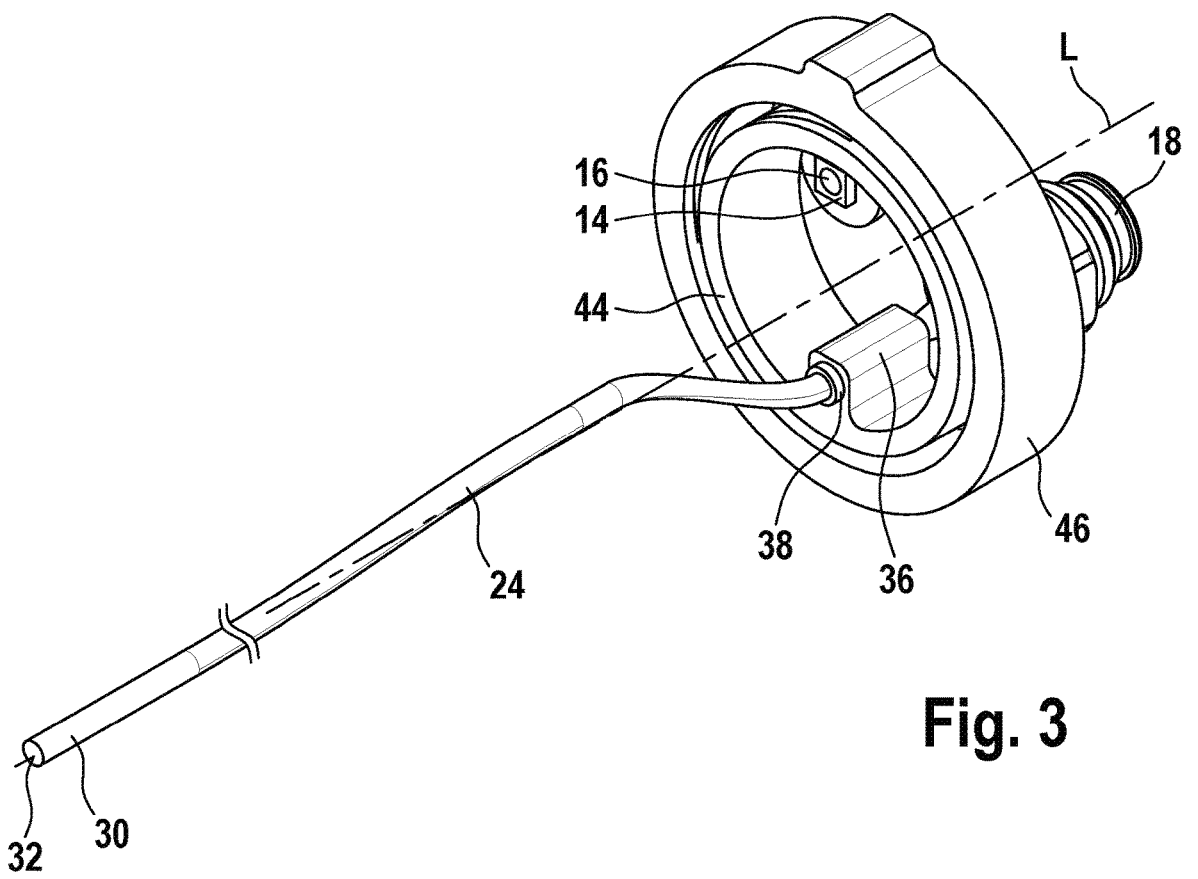
FIG. 3 shows the embodiment without a housing, with rings in a second position, in a first perspective view.
Figure 4:
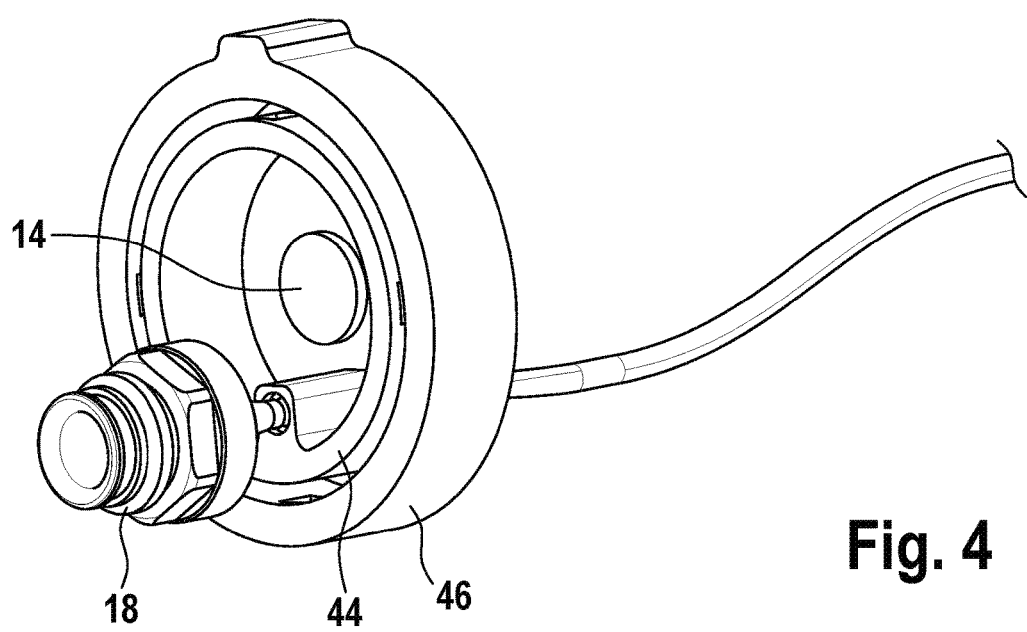
FIG. 4 shows the embodiment without a housing in a second perspective view.

The third interface 28 is displaceably arranged relative to the first and the second interface 16, 22 such that the third interface 28 can receive light from the first interface 16 in a first position (see FIG. 9) and receive light from the second interface 22 in a second position (see FIG. 3).

The first end 26 is linearly displaceably held in a guide 36. To this end, the first end 26 comprises a sleeve 38 and the sleeve 38 is linearly displaceably held in the guide 36. In this case, the guide 36 and the sleeve 38 have a cylindrical embodiment. Moreover, see FIGS. 11A and 11B, the sleeve 38 may comprise a flange 40 which forms a stop for a displacement of the sleeve 38, in this case a stop in the distal direction.

Figure 2:
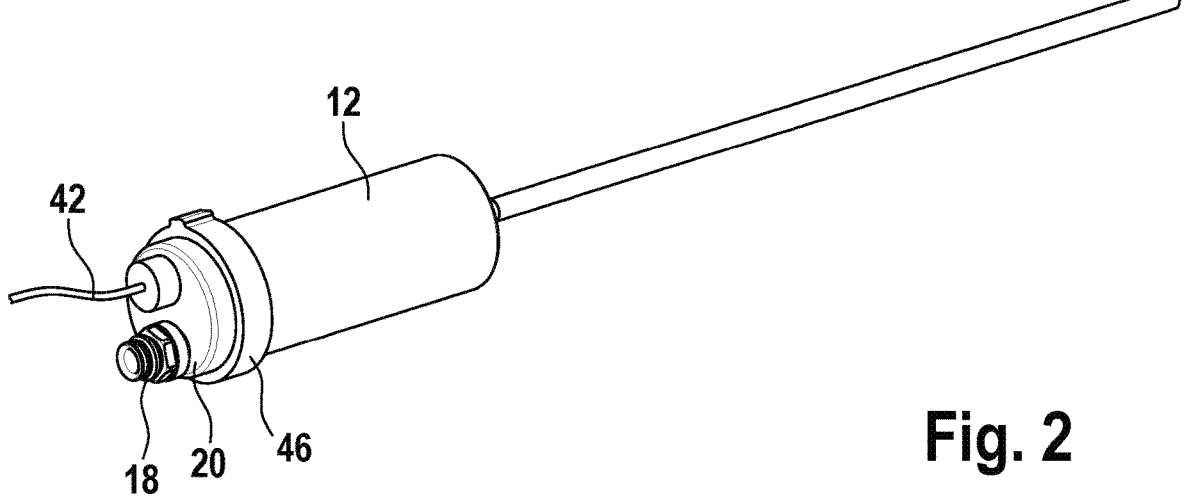
FIG. 2 shows the embodiment in a second perspective view.

As indicated in FIG. 2, the light source 14 is supplied with power via a power supply 42, which is guided from outside of the housing 12 through the housing wall 20 of the housing 12.

Figure 5:
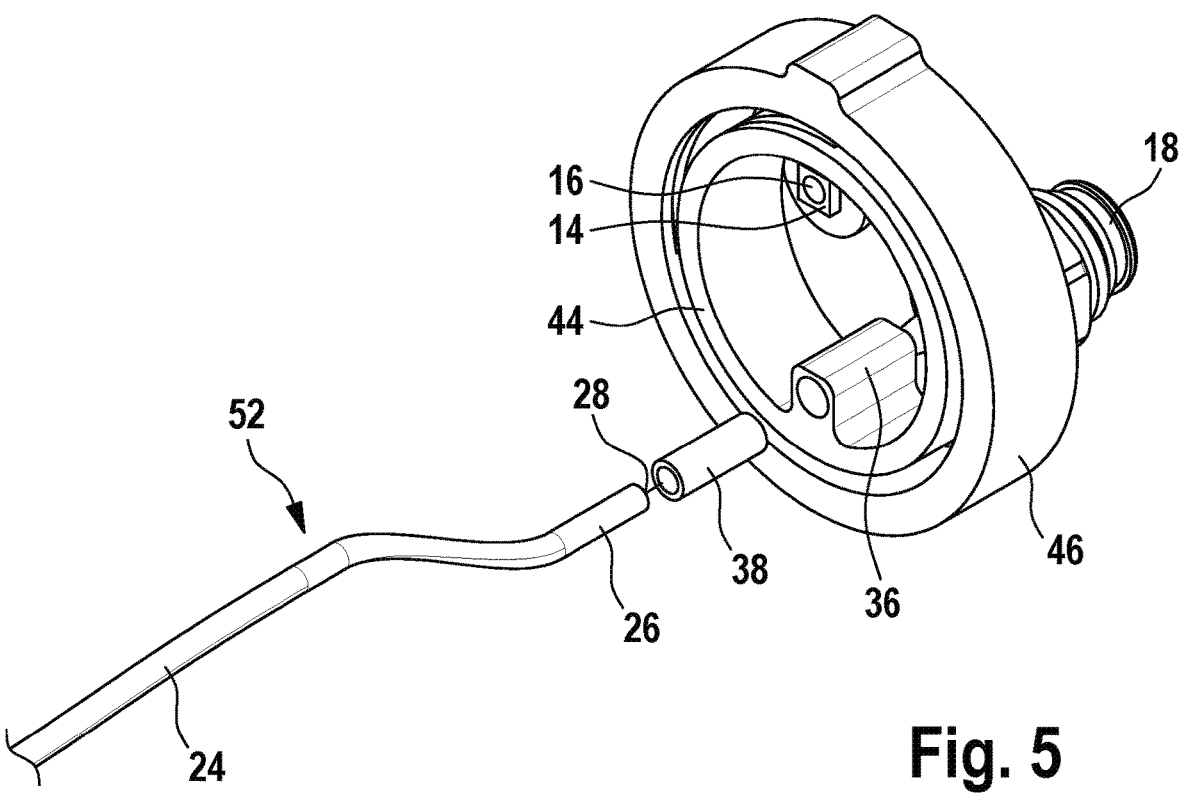
FIG. 5 shows the view of FIG. 3 in a partly exploded illustration.
Figure 6:
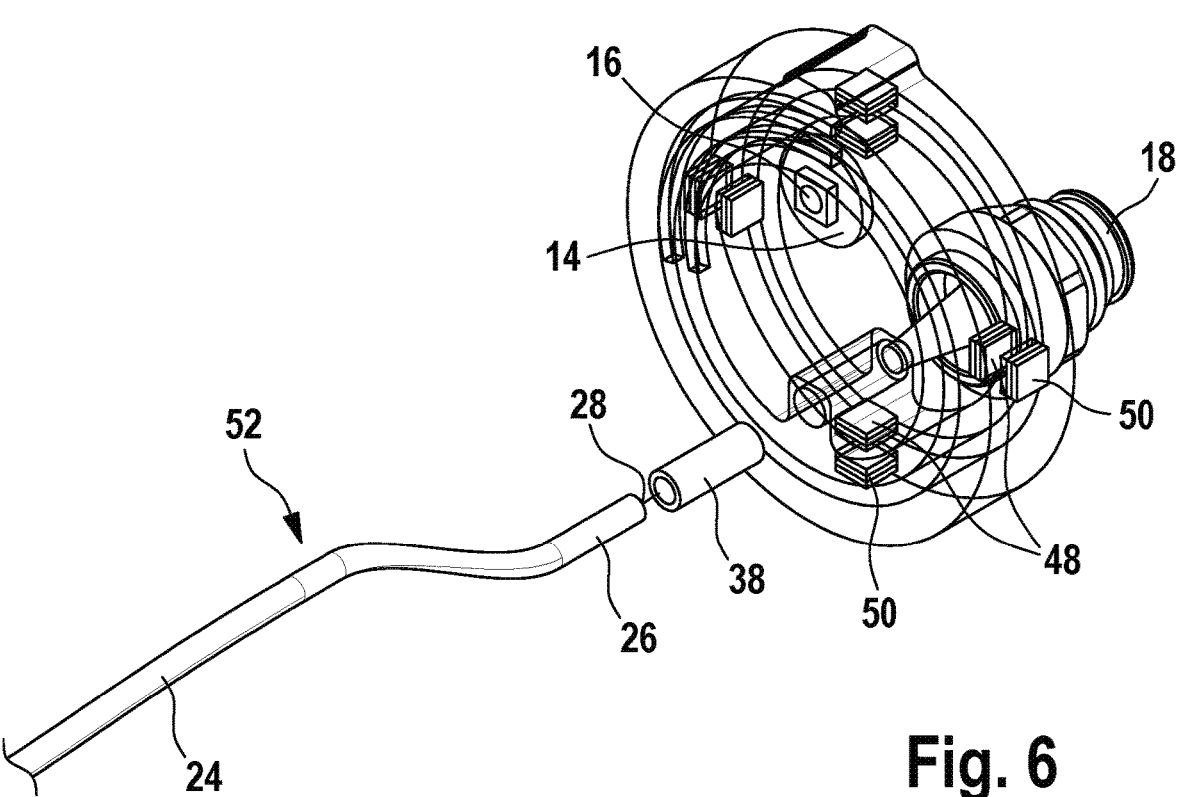
FIG. 6 shows the view of FIG. 5 as a wire model.
Figure 7:
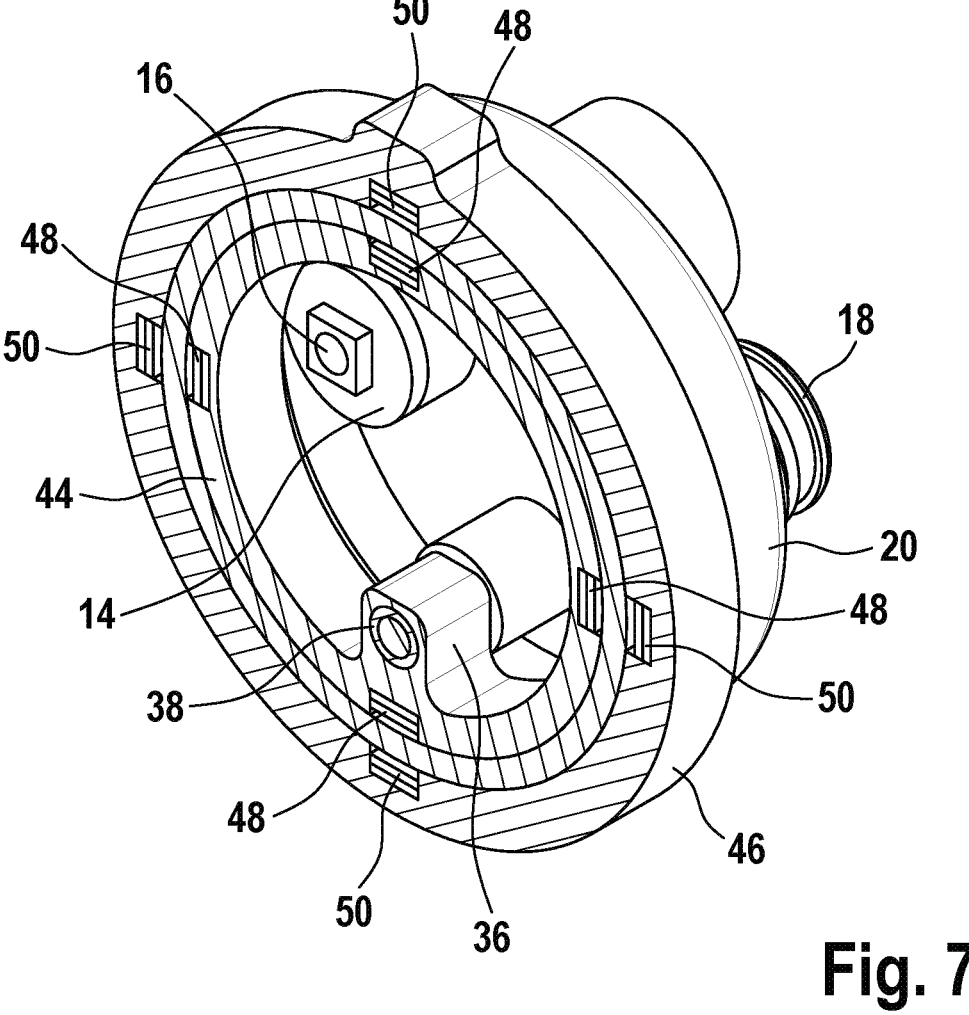
FIG. 7 shows a section through the proximal end of the embodiment.

Proceeding from FIGS. 5, 6 and 7, explanations are provided as to how the switchover between the one light source 14 and the light supply 18 can be implemented. The first end 26 is arranged on an inner ring 44 which is within the housing 12 and rotatably arranged about a longitudinal axis L of the endoscope 10. In this case, the longitudinal axis L of the endoscope 10 can be the longitudinal central axis of the endoscope 10 in some configurations.

The endoscope 10 further comprises an outer ring 46 which is arranged outside of the housing 12 and rotatably arranged about the longitudinal axis L of the endoscope 10. At least one first magnet 48 is arranged on the inner ring 44, and at least one second magnet 50 is arranged on the outer ring 46. In this case, four magnets 48, 50 are present in each case. The first magnets 48 and the second magnets 50 interact in such a way that a rotation of the outer ring 46 can bring about a rotation of the inner ring 44. In the process, as shown here, the attractive force between opposite poles can be used; however, it is alternatively also possible to use the repulsive force of the same poles.

Figure 8:
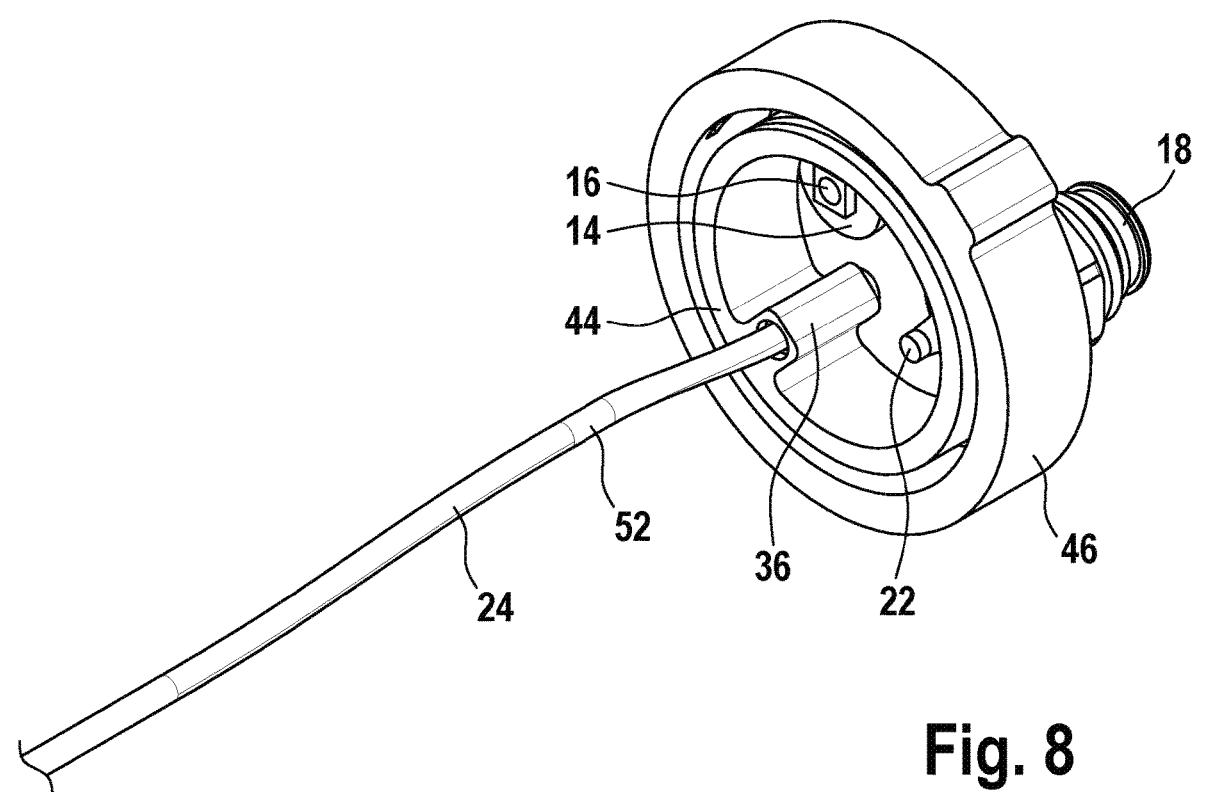
FIG. 8 shows the embodiment without the housing, with the rings in an intermediate position.
Figure 9:
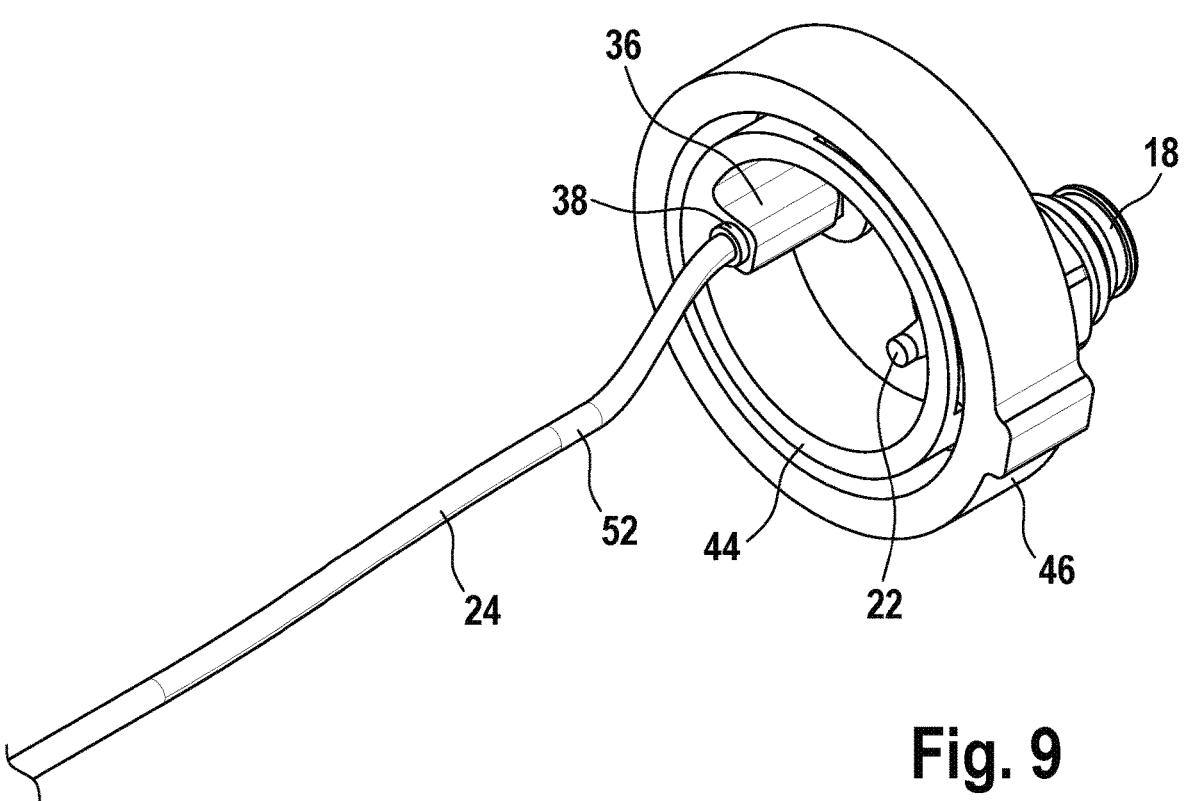
FIG. 9 shows the embodiment without the housing, with the rings in a first position.

FIGS. 8 and 9 show how the magnetic interaction of the first magnets 48 and the second magnets 50 lead in the case of a rotation of the outer ring 46 to a corresponding displacement of the inner ring 44, and hence of the end 26. Thus there can be an operation without the hermetic seal of the housing 12 being weakened, despite the housing 12 being located between the inner ring 44 and the outer ring 46.

In this case, it is evident from FIG. 8 that the end 26 with the sleeve 38 has been displaced in the proximal direction. This enables a displacement of the end 26, with the result that the light guide 24 can be fastened to the housing at a fixed point 52 but there can nevertheless be a length compensation of the light guide 24 in the event of a rotation of the inner ring 44.

FIG. 10 shows that the housing 12 or the housing wall 20 has two inwardly directed first stops 54. The first stops 54 interact with a first protrusion 56 on the inner ring 44 and limit a displacement of the inner ring 44 to a first angular range a.

The housing 12 or the housing wall 20 further comprises two outwardly directed second stops 58 which interact with a second protrusion 60 on the outer ring 46 and limit a displacement of the outer ring 46 to a second angular range B, with the second angular range being greater than the first angular range.

The second protrusion 60 comprises a catch 62 which is pressed inwardly against the housing 12 by means of a spring 61. The catch 62 interacts with at least one cutout 64 in the housing 12, in order to detachably fix the outer ring 46 in at least one defined position. In this case, the catch 62 is designed as a ball catch.

FIGS. 11A and 11B depict two exemplary situations, as may arise in the case of a rotation of the inner ring 44. In this case, FIG. 11A may correspond to the situation as shown in FIG. 3 or FIG. 9, and FIG. 11B may correspond to the situation as shown in FIG. 8.

In FIG. 11A, the path from the fixed point 52 to the entrance into the guide 36 is slightly longer than in FIG. 11B. In FIG. 11A, the flange 40 rests against the proximal end of the guide 36. In FIG. 11B, the flange 40 has detached from the sleeve 36. This can take account of a shortening of the path and a mechanical resistance as a result of a compression or bending of the light guide 24 can be avoided.

Figure 12:
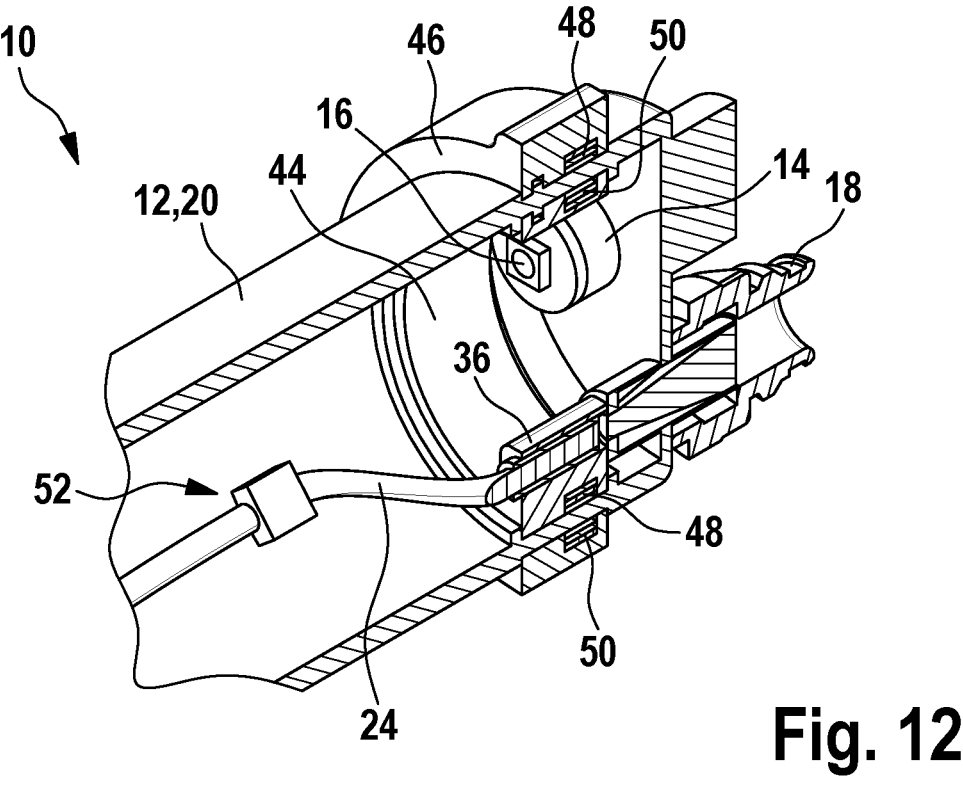
FIG. 12 shows a sectional illustration of the embodiment along the longitudinal axis, with the rings in the second position.
Figure 13:
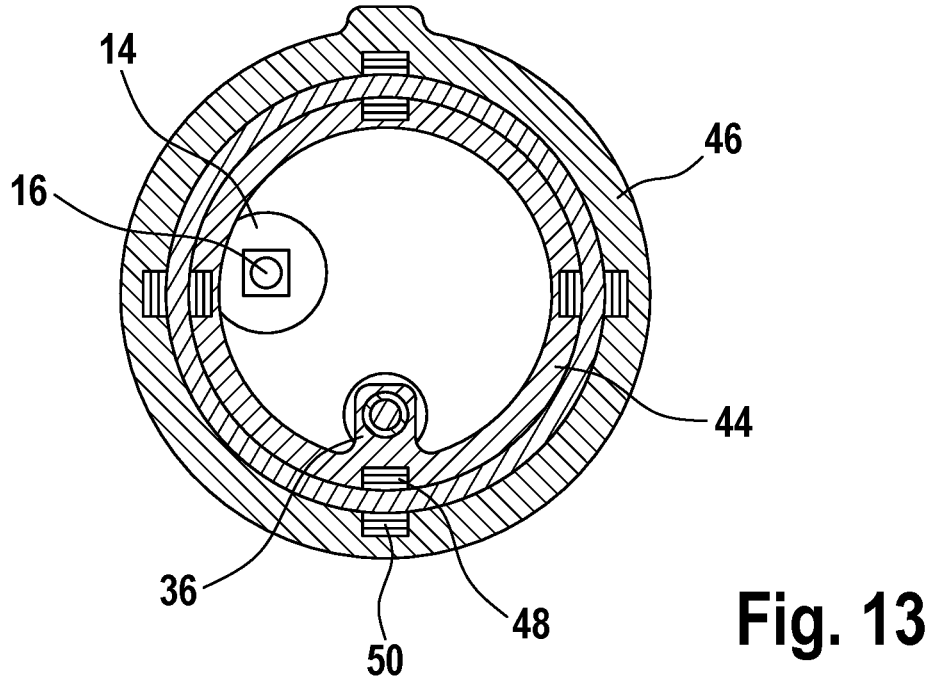
FIG. 13 shows a plan view of the rings in the second position.

FIG. 12 shows a sectional illustration of the embodiment along the longitudinal axis L with the rings in the second position, and FIG. 13 shows a plan view of the rings in the second position. The third interface 28 is likewise in its second position here.

Figure 14:
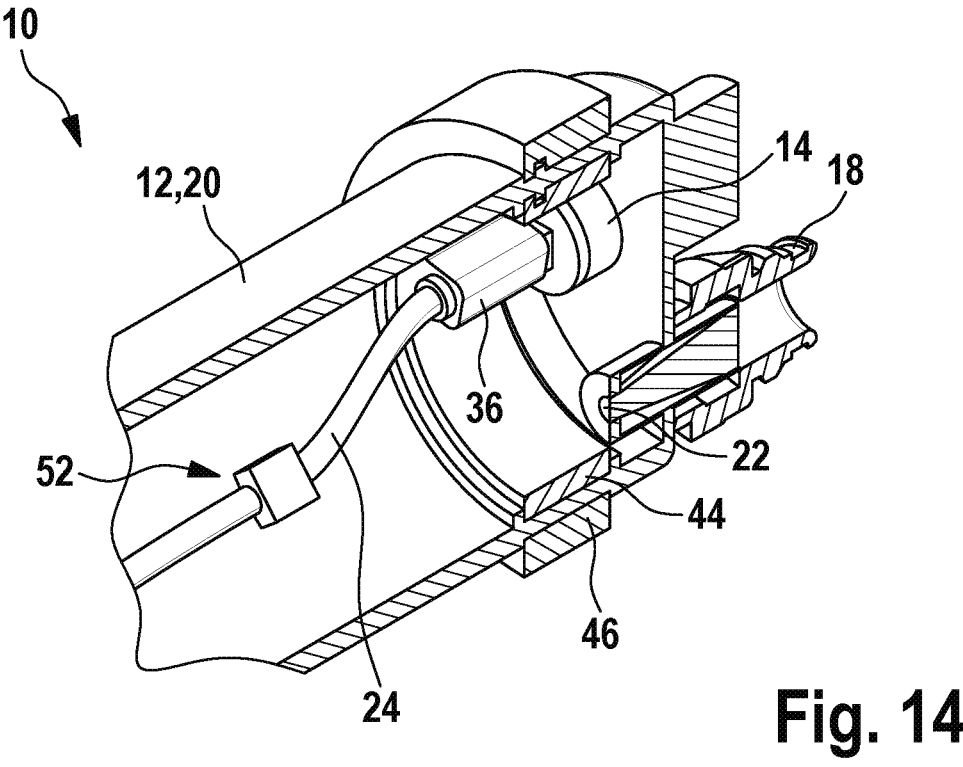
FIG. 14 shows a sectional illustration of the embodiment along the longitudinal axis, with the rings in the first position.
Figure 15:
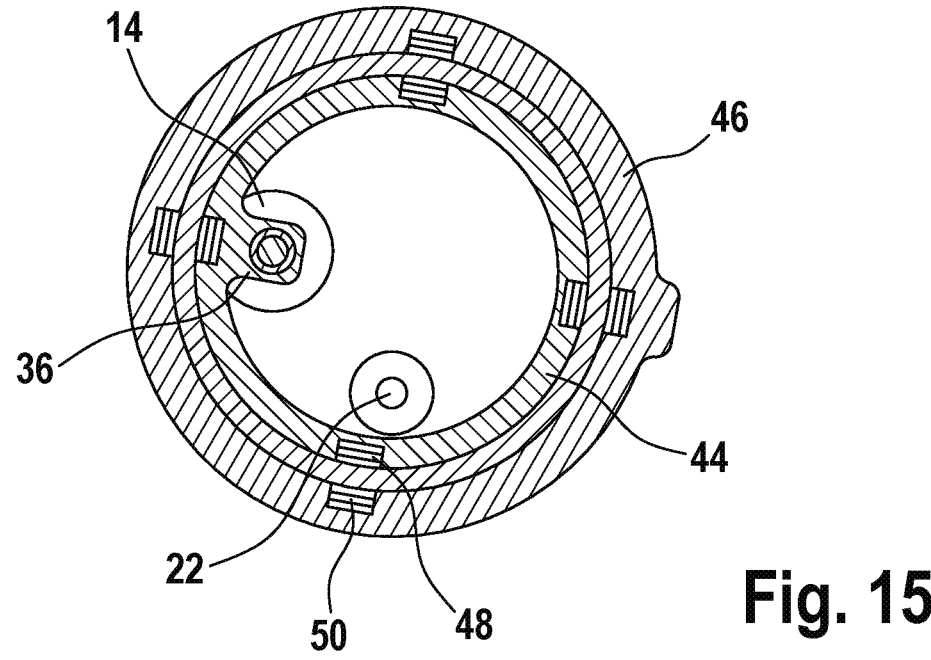
FIG. 15 shows a plan view of the rings in the first position.

FIG. 14 shows a sectional illustration of the embodiment along the longitudinal axis L with the rings in the first position, and FIG. 15 shows a plan view of the rings in the first position. The third interface 28 is likewise in its first position here.

The invention claimed is:

1. An optical instrument comprising:
a housing;
a light source disposed within the housing and designed to create a first light flux that emerges at a first interface within the housing;
a light supply from outside of the housing is guided through a housing wall of the housing and designed to guide a second light flux from outside of the housing into an interior of the housing and allow said light flux to emerge at a second interface within the housing; and
a light guide disposed within the housing and designed to receive light at a first end via a third interface and allow said light to emerge at a second end via a fourth interface at a distal end of the optical instrument, with the third interface being displaceably arranged relative to the first and the second interface such that the third interface can receive light from the first interface in a first position and receive light from the second interface in a second position.

2. The optical instrument as set forth in claim 1, wherein the first end of the light guide is linearly displaceably held in a guide.

3. The optical instrument as set forth in claim 2, wherein the first end comprises a sleeve and the sleeve is linearly displaceably held in the guide.

4. The optical instrument as set forth in claim 3, wherein the guide and the sleeve are cylindrical.

5. The optical instrument as set forth in claim 2, wherein the guide and the sleeve are cylindrical.

6. The optical instrument as set forth in claim 5, wherein the sleeve comprises a flange which forms a stop for a displacement of the sleeve.

7. The optical instrument as set forth in claim 1, wherein the light source is supplied with power via a power supply, which is guided from outside of the housing through the housing wall of the housing.

8. The optical instrument as set forth in claim 1, wherein the first end is arranged within the housing on an inner ring that is rotatably arranged about a longitudinal axis of the optical instrument.

9. The optical instrument as set forth in claim 8, further comprising including an outer ring that is arranged outside of the housing and rotatably arranged about the longitudinal axis of the optical instrument, with at least one first magnet being arranged on the inner ring, at least one second magnet being arranged on the outer ring, and the first magnet and the second magnet inter-acting such that a rotation of the outer ring can bring about a rotation of the inner ring.

10. The optical instrument as set forth in claim 9, wherein the housing further includes two inwardly directed first stops, which interact with a first protrusion on the inner ring and limit a displacement of the inner ring to a first angular range, and two outwardly directed second stops, which interact with a second protrusion on the outer ring and limit a displacement of the outer ring to a second angular range, the second angular range being greater than the first angular range.

11. The optical instrument as set forth in claim 10, wherein the second protrusion has a catch which is pressed inwardly against the housing by means of a spring, and this catch interacts with at least one cutout in the housing in order to detachably fix the outer ring in at least one defined position.

12. The optical instrument as set forth in claim 1, wherein the light supply and/or the light guide includes an optical waveguide.

* * * * *